United States Patent [19]
Lorenzi et al.

[11] 4,035,721
[45] July 12, 1977

[54] SYSTEM AND METHOD USING MAGNETIC TAPE FOR TESTING OF SMALL CYLINDRICAL PARTS

[75] Inventors: Donald E. Lorenzi, Des Plaines; Kenneth W. Schroeder, Arlington Heights; Richard C. Sabielny, McHenry, all of Ill.

[73] Assignee: Magnaflux Corporation, Chicago, Ill.

[21] Appl. No.: 566,420

[22] Filed: Apr. 9, 1975

[51] Int. Cl.² .................................. G01R 33/12
[52] U.S. Cl. ................................ 324/37
[58] Field of Search ..................... 324/37, 38

[56] References Cited
U.S. PATENT DOCUMENTS

| | | | |
|---|---|---|---|
| 2,648,435 | 8/1953 | Kodis | 324/37 |
| 3,262,053 | 7/1966 | Nasir et al. | 324/37 |
| 3,341,771 | 9/1967 | Crouch et al. | 324/38 |
| 3,760,263 | 9/1973 | O'Connor et al. | 324/37 |

FOREIGN PATENT DOCUMENTS

| | | | |
|---|---|---|---|
| 174,415 | 9/1964 | U.S.S.R. | 324/37 |
| 179,071 | 4/1966 | U.S.S.R. | 324/37 |
| 241,783 | 8/1969 | U.S.S.R. | 324/37 |

*Primary Examiner*—Robert J. Corcoran
*Attorney, Agent, or Firm*—Brezina & Lund

[57] ABSTRACT

The invention relates to a system and method of testing small cylindrical parts wherein a part is journalled for free rotation about a substantially stationary axis with one side of the part being frictionally engaged with a magnetic tape moved longitudinally to rotate the part and to transfer a magnetic flux pattern at the surface of the part to the tape. Important features relate to the provision of engagement means for obtaining non-skid intimate contact between the tape and the part, to the application of a biasing field to the tape at the area of interengagement between the tape and the part and to the manner of supporting the part.

5 Claims, 2 Drawing Figures

SYSTEM AND METHOD USING MAGNETIC TAPE FOR TESTING OF SMALL CYLINDRICAL PARTS

This invention relates to a system and method of magnetic testing and more particularly to a system and method which permits small cylindrical parts to be readily and quickly tested while obtaining a high sensitivity to inhomogeneities in the part, such as seams of shallow depth.

BACKGROUND OF THE INVENTION

Eddy current testing arrangements can be used for the testing of many types of parts but the testing of the entire surface of a part generally requires a substantial amount of time and for this reason, eddy current testing not always is satisfactory, especially in the testing of small cylindrical parts. Also, eddy current inspection does not readily adapt itself to automatic inspection.

Various arrangements have heretofore been proposed for magnetic testing of parts by effecting engagement between a surface of a part and a magnetic tape or sheet with the part being magnetized prior to or during such engagement, a magnetic flux pattern of the surface of the part being transferred to the magnetic tape or sheet. The flux pattern on the tape or sheet is then detected by scanning with a reproducing head or by applying magnetic particles over the surface of the tape or sheet.

Included in the prior art disclosures is that of the Kodis U.S. Pat. No. 2,648,435 wherein a magnetized cylindrical specimen is rolled between a portion of a magnetic inspection belt moving in one direction and a conveyor belt moving in an opposite direction moving at a greater speed, the magnetic pattern recorded on the inspection belt being detected by a magnetic head. Other patents disclose arrangements in which a tape is pressed against a part surface with the tape being moved by engagement with a moving part or with the part being stationary and the tape being carried and driven in a manner to move along or around the part. For example, the O'Connor et al U.S. Pat. No. 3,760,263 discloses an arrangement in which a magnetic tape is entrained for movement on a support structure with the support structure and an elongated object being tested being moved relative to one another about a longitudinal axis of the object, preferably with there being a generally helical path of movement of the area of interengagement between the tape and the object. Other examples are disclosed in the Nasir et al U.S. Pat. No. 3,262,053, the Crouch et al U.S. Pat. No. 3,341,771, the Mandula U.S. Pat. No. 3,593,120 and the Forster U.S. Pat. No. 3,656,054.

The arrangement of the O'Connor et al patent is highly advantageous in the testing of large parts and especially parts such as square billets but would not be generally satisfactory for the testing of roller bearings or other small parts. The arrangement of the Kodis patent poses serious problems especially with respect to accurately controlling movement of the specimen between the inspection and conveyor belts and proper engagement of the part with the inspection belt. The other prior patents also have serious limitations with respect to the applicability to the testing of small parts.

SUMMARY OF THE INVENTION

This invention was evolved with the general object of providing a system and method for rapid testing of cylindrical parts, especially roller bearings or other small parts, with a high degree of sensitivity with respect to detection of longitudinal seams of other inhomogeneities in such parts.

According to an important feature of the invention, a part is journalled for free rotation about a substantially stationary axis coincident with the axis of a cylindrical surface portion of the part and for frictional engagement of one side portion of the cylindrical surface portion of the part with one surface of a magnetic tape, with the tape being moved longitudinally to effect rotation of the part about the substantially stationary axis through the frictional engagement between the tape and the one side portion of the cylindrical surface portion of the part. During each revolution of the part, the magnetic flux pattern at the outer cylindrical surface portion of the part is transferred to a segment of the tape having a length equal to the circumferential length of the cylindrical surface portion. Through the journalling of the part for free rotation about a substantially stationary axis and the drive of the part through frictional engagement with the tape, an accurate transfer of the flux pattern to the tape can be obtained, even with parts such as roller bearing having a quite small diameter.

According to a very important specific feature, engagement means are provided opposite the side portion of the cylindrical surface portion of the part for engagement of the opposite surface of the tape, with spring means being provided for exerting a squeezing force on the tape between the engagement means and the one side portion of the cylindrical surface portion to obtain intimate non-skid frictional engagement between the tape and the part, further facilitating the accurate transfer of the flux pattern to the tape.

Another very important specific feature relates to the provision of magnetic biasing means associated with the engagement means for applying a magnetic biasing field to the portion of the tape engaged with the part. The magnetic biasing means, in one embodiment, comprises magnet means for applying a uni-directional field of substantially constant intensity, preferably using a permanent magnet. In another embodiment, an alternating magnetic field is applied, preferably using a magnetic head having a narrow gap extending in parallel relation to the axis of the part and transverse to the direction of movement of the tape. With either biasing arrangement, the optimum results are obtained by using the proper strength of the biasing field and in the case of the alternating field, the gap of the magnetic head and the thickness of the tape are small enough to confine the biasing field to the area of interengagement between the tape and the part. This is found to be very important in preventing an erasure effect.

With the magnetic biasing and especially with the alternating biasing field, it is possible to obtain a high degree of sensitivity especially with respect to seams of shallow depth, and in this connection, the defects in roller bearings and similar parts which are apt to occur and which may cause failure of the part are generally in the form of seams parallel to the axis of the part.

The flux pattern of the tape can be readily detected using a reproducing head engaged with the tape and by using a reproducing head having a narrow gap extending transversely relative to the tape, a high degree of sensitivity to seams or similar defects can be obtained.

A further feature relates to the manner of support of the part, preferably comprising a bearing member having a frusto-cylindrical concave bearing surface with a radius approximately equal to that of the outer cylindrical surface of the part and engageable with the side of the part opposite the side engaged with the tape. This arrangement accurately positions the part and also permits ready insertion and removal of the part for rapid inspection.

This invention contemplates other objects, advantages and features which will become more fully apparent from the following detailed description taken in conjunction with the accompanying drawings.

DESCRIPTION OF PREFERRED EMBODIMENTS

Figure 1:
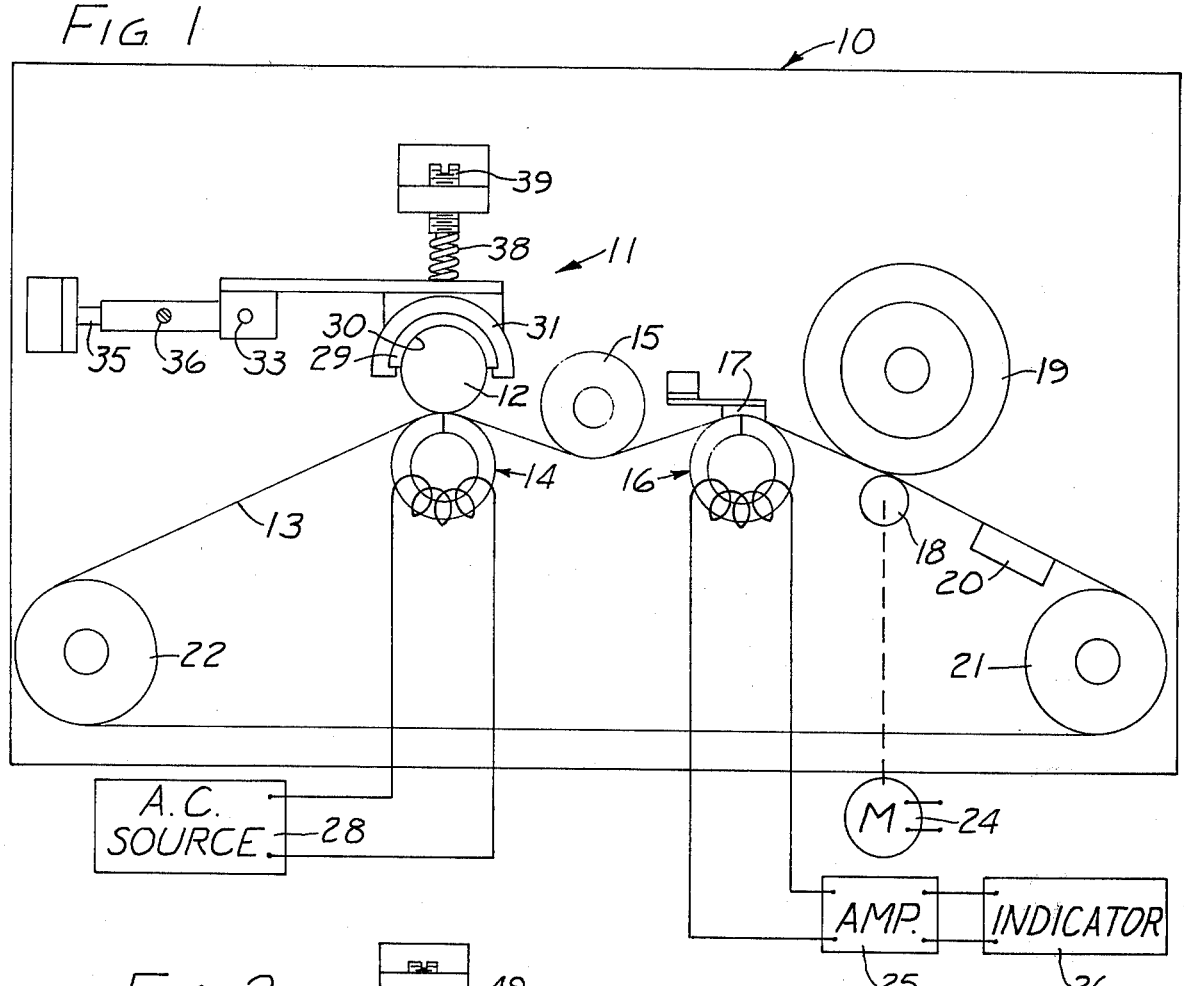
FIG. 1 is an elevational view, partially diagrammatic, illustrating apparatus for magnetic testing, constructed in accordance with the invention.

Reference numeral 10 generally designates apparatus constructed in accordance with the principles of this invention, especially designed for the magnetic testing of small cylindrical parts, such as roller bearings, for example, which may be magnetized by passing a current axially therethrough to create a residual magnetic flux pattern on the outer cylindrical surface thereof, leakage fields being produced across inhomogeneities such as axially extending seams.

The apparatus 10 comprises a structure 11 for supporting and journalling a cylindrical part 12 for free rotation about a substantially stationary axis coincident with the axis of the outer cylindrical surface of the part 12. An endless loop of magnetic tape 13 passes between the lower side of the part 12 and a magnetic head 14 used for applying a biasing field as hereinafter described and also forming engagement means for obtaining intimate non-skid frictional contact between the tape 13 and the lower side of the part 12. The tape 13 extends under an idler roller 15 thence between the upper side of a read head 16 and a pressure pad 17, thence between a drive capstan 18 and a pinch roller 19, thence over an erase magnet 20, and thence about idler rollers 21 and 22 back to the biasing head 13 and part 12.

As diagrammatically illustrated, the capstan 18 is driven in a clockwise direction by means of a motor 24 to move the upper portion of the tape longitudinally to the right as viewed in FIG. 1. Through frictional engagement between the tape and the lower side of the part 12, the part 12 is rotated in a counter-clockwise direction and during each revolution of the part 12, the magnetic flux pattern on the outer cylindrical surface of the part is recorded on a segment of the magnetic tape 13 having a length equal to the circumference of the outer cylindrical surface of the part 12. When such segment of the tape passes over the read head 16, electrical signals are developed which are applied through an amplifier 25 to an indicator 26 which may be in the form of an oscilloscope, for example and/or may include a threshold circuit and means for energizing a lamp or other signalling device when the signal produced by the read head 16 has a magnitude greater than a certain value.

The biasing head 14 is connected to an AC source 28 which preferably supplies current at a relatively high frequency, 50 kHz, for example, and the biasing head 14 applies an alternating field to the portion of the tape 13 engaged with the part 12 to lower the inherent magnetic threshhold of the tape and to greatly increase the sensitivity of recording on the tape of low leakage field intensities such as produced by seams of shallow depth on the surface of the part 12.

It is found that the alternating biasing field must be confined to the area of interengagement between the tape and the part because if it is not, an alternating field of substantial intensity is applied to the tape alone as it leaves the area of interengagement, resulting in erasure of the recording on the tape. It is further found that to confine the field to the area of interengagement requires use of a relatively narrow gap in the head 14 and the use of a thin tape. For example, tests have been performed on a part 12 in the form of a hardened steel bearing roll having a diameter of 0.355 inches, the dimensions of the parts of the apparatus being in approximately the same proportion as illustrated in the drawings. The biasing head was of a type used for recording and reproducing or erasing in conventional tape recorders having a gap of on the order of 0.001 inches or less. With a thick tape of red oxides and neoprene having a thickness of 0.08 inches the fringing alternating biasing field level was sufficiently high at the point of tape unwrap to produce tape erase. However, using a very thin mylar base audio recording tape, having a thickness of approximately 0.001 inches, excellent results were obtained.

The part support and journalling structure 11 comprises a member 29 having a frusto-cylindrical concave surface 30 with a radius approximately equal to the radius of the cylindrical surface of a part 12, the surface 30 being engaged with the upper side of the part 12, i.e. the side opposite that engaged with the tape 13. Member 29 is carried by a holder 31 on the end of an arm 32 which is pivotally connected by a pin 33 to a sleeve 34 slidably supported on a fixed rod 35, a set screw 36 being provided to fix the position of the member 34 on the rod 35. The member 29 is urged downwardly by means of a compression spring 38 engaged with the arm 32, a set screw 39 being provided to adjust the pressure exerted by the spring 38. The pressure applied should be sufficient to obtain intimate non-skid engagement between the tape 13 and the part 12, while allowing free rotation of the part 12 relative to the bearing surface 30 of the member 29.

It is very important that the area of interengagement between the part 12 and the tape 13 be accurately aligned with the gap of the biasing head 14 and the position of this member 34 on the support rod 35 is adjustable for this purpose.

Figure 2:
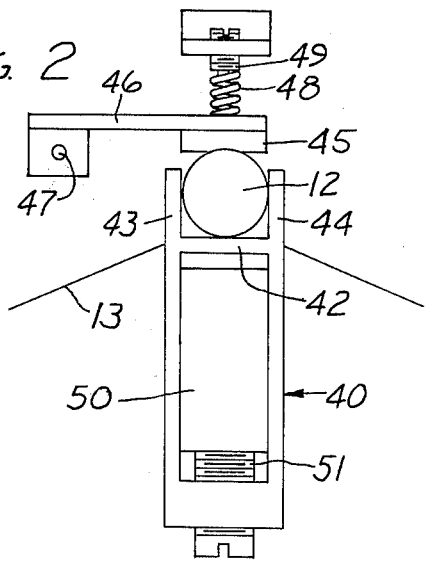
FIG. 2 illustrates modified part support and biasing means.

FIG. 2 illustrates a modified arrangement for supporting the part 12 and applying a biasing field to the tape 13. In this arrangement, a jig 40 is provided having a horizontally extending portion 42 the upper surface of which engages the lower surface of the tape 13, and having a pair of upstanding portions 43 and 44 for engaging the left and right sides of the part 12 and cradling the part 12 for rotation about its axis, suitable slots being provided in the portions 43 and 44 for passage of the tape 13. The upper side of the part 12 is engaged by a resilient pressure pad 45 carried by an arm 46 pivotally supported by a pin 47, the arm 46 being engaged by a compression spring 48 to apply a pressure controlled by a set screw 49.

The jig 40 carries a permanent magnet 50 the vertical position of which is controllable by a set screw 51. The magnet 50 supplies a uni-directional bias field of constant intensity and no erasure phenomenon is produced so that the tape can be relatively thick and the field does not need to be restricted to the area of interengagement between the tape and the part. The magnitude of the field is, however, somewhat critical, and by way of example, in testing a hardened steel bearing roll having a diameter of 0.355 inches and a length of 0.355 inches, an endless belt or tape, 0.08 inches thick by 7/16 inches wide and made of red oxide and neoprene was used. It was found that the biasing field level, measured at the tape surface opposite the magnet with the test part removed, should preferably be between 200 and 300 oersteds, and most preferably about 250 oersteds.

Residual magnetization is preferably employed. For a hardened steel bearing roll, 0.355 inches in diameter by 0.355 inches in length, a current shot of approximately 600 amperes with circular magnetization is required for best results. Very short duration half wave direct current shots, obtained by half wave rectification of a 60 Hz current, have been found to be just as effective as long duration full wave direct current shots. It was also found that current shots in excess of 600 amperes did not significantly increase the level to which the parts were residually magnetized.

The read head 16 is preferably of the type used in conventional tape recorders, except that for the purpose of inspecting longer parts, wider heads may be used.

An important aspect of the inventon is that there is a high degree of sensitivity to seams which extend axially on the outer cylindrical surface of a part, such seams being a serious problem in parts such as roller bearings and the like.

It is further noted that although the tape 13 is shown in the form of an endless loop, an arrangement can be provided for unwinding the tape from a supply reel and winding it on a take-up reel as in a conventional tape recorder. With such an arrangement, the test pattern of a series of test parts can be recorded and stored and thereafter run through reproducing equipment for analysis, whenever desired. Also, the part can be magnetized during engagement with the tape, rather than with residual magnetization. In the case of long parts, a plurality of biasing heads may be used and a plurality of reproducing heads may be employed in such cases or to detect cracks at various angles. In place of or in addition to drive from frictional engagement with the tape, a synchronized drive of the part may be employed.

It will be understood that other modifications and variations may be effected without departing from the spirit and scope of the novel concepts of this invention.

We claim as our invention:

1. In a system for testing small metal parts having outer cylindrical surfaces, part support and journalling means for journalling a part for free rotation about a first axis coincident with the axis of the cylindrical surface thereof, pressure applying means in spaced relation to said first axis for engaging one surface of a magnetic tape to press the opposite surface of the tape into engagement with said cylindrical surface of said part, tape guide and drive means including an idler roller and a drive capstan journalled on axes in spaced parallel relation to each other and to said first axis for engagement with portions of the tape spaced longitudinally in opposite directions from the portion of the tape engaged with said cylindrical surface of the part, a pinch roller for pressing the tape into frictional engagement with said capstan, and means for driving said capstan to move the tape longitudinally from said idler roller thence between said pressure appplying means and said cylindrical surface of the part and thence between said capstan and said pinch roller, said pressure applying means being in slidable engagement with said one surface of the tape to permit longitudinal movement of the tape relative thereto while being operative to press said opposite surface of the tape into firm frictional engagement with said cylindrical surface of the part to drivably rotate the part about said first axis solely from frictional engagement with the tape and to operate during each revolution of the part to transfer a magnetic flux pattern at said outer cylindrical surface of the part to a segment of said tape having a length equal to the circumference of said cylindrical surface, said pressure-applying means comprising engagement means engaging said one surface of the magnetic tape, spring means acting between said part support and journalling means and said engagement means for exerting a squeezing force on the tape between said engagement means and said cylindrical surface of the part to obtain intimate non-skid frictional engagement between the tape and said cylindrical surface of the part, and magnetic biasing means associated with engagement means for applying a magnetic biasing field to the portion of said tape engaged with said cylindrical surface of the part, said magnetic biasing means comprising a magnetic head also forming said engagement means and having a narrow gap extending transversely relative to the direction of movement of the tape with the width of said gap and the thickness of the tape being small enough to confine the magnetic biasing field to the area of interengagement between the tape and said cylindrical surface of the part and to minimize the field applied to the tape alone as it leaves said area of interengagement to thereby minimize erasure of information recorded on the tape.

2. In a system as defined in claim 1, a reproducing head engagable with the tape at a point spaced in the direction of movement of the tape from the point of engagement of the tape with the part, said reproducing head having a narrow gap transverse to the direction of movement of the tape and at substantially the same angle to the direction of movement of the tape as the angle between the gap of said magnetic head of said biasing means and the tape.

3. In a system as defined in claim 2, both of said gaps being at substantially a right angle to the direction of longitudinal movement of the tape and in parallel relation to said first axis.

4. In a system as defined in claim 1, means for adjusting the relative position of said part support and journalling means and said magnetic head to accurately position said gap at the area of interengagement between the tape and said cylindrical surface of the part.

5. In a system as defined in claim 1, said part support and journalling means comprising a bearing member having a frusto-cylindrical concave bearing surface having a radius approximately equal to that of said outer cylindrical surface of the part and engagable with a side portion of said cylindrical surface of the part opposite the portion thereof engaged by the tape.

* * * * *